(12) United States Patent
Hanebuchi

(10) Patent No.: US 7,255,440 B2
(45) Date of Patent: Aug. 14, 2007

(54) KERATECTOMY DATA DETERMINING DEVICE AND KERATECTOMY DATA DETERMINING PROGRAM

(75) Inventor: Masaaki Hanebuchi, Nukata-gun (JP)

(73) Assignee: Nidek Co., Ltd. (JP)

( * ) Notice: Subject to any disclaimer, the term of this patent is extended or adjusted under 35 U.S.C. 154(b) by 307 days.

(21) Appl. No.: 10/476,246

(22) PCT Filed: Jun. 3, 2002

(86) PCT No.: PCT/JP02/05452

§ 371 (c)(1),
(2), (4) Date: Oct. 30, 2003

(87) PCT Pub. No.: WO02/098335

PCT Pub. Date: Dec. 12, 2002

(65) Prior Publication Data

US 2004/0135969 A1    Jul. 15, 2004

(30) Foreign Application Priority Data

Jun. 1, 2001    (JP) .............................. 2001-167325

(51) Int. Cl.
*A61B 3/10*    (2006.01)
(52) U.S. Cl. ...................... 351/212; 351/208; 351/209; 351/211; 351/216
(58) Field of Classification Search ......... 351/200–247
See application file for complete search history.

(56) References Cited

U.S. PATENT DOCUMENTS

| | | | |
|---|---|---|---|
| 4,315,672 A | * | 2/1982 | Muller et al. ................ 351/212 |
| 4,666,269 A | * | 5/1987 | Nakamura et al. ........... 351/212 |
| 5,231,674 A | * | 7/1993 | Cleveland et al. ........... 382/117 |
| 6,033,075 A | * | 3/2000 | Fujieda et al. ............... 351/212 |
| 6,416,179 B1 | * | 7/2002 | Lieberman et al. ......... 351/212 |

(Continued)

FOREIGN PATENT DOCUMENTS

EP    0 836 830 A1    4/1998

(Continued)

OTHER PUBLICATIONS

PCT International Search Report for PCT/JP02/05432 mailed on Sep. 24, 2002.
International Search Report for PCT/JP02/05452 Sep. 24, 2002.

*Primary Examiner*—Brian L. Casler
*Assistant Examiner*—Sanjay Cattungal
(74) *Attorney, Agent, or Firm*—Rader Fishman & Grauer PLLC; Ronald P. Kananen

(57) ABSTRACT

The purpose of the present invention is to provide a corneal-ablation-data determining apparatus and a corneal-ablation-data determining program capable of controlling corneal ablation amount distribution and expanding ablation applicability. In the present invention, the corneal-ablation-data determining apparatus for use in keratorefractive surgery for ablating a corneal surface to correct a refractive error has input means for inputting measurement data on any one of wavefront aberration distribution and refractive power distribution of a patient's eye, decentering means for decentering a reference axis being a calculation reference for a corneal ablation amount, and calculation means for obtaining the corneal ablation amount based on the measurement data and data on eccentricity of the reference axis.

3 Claims, 6 Drawing Sheets

U.S. PATENT DOCUMENTS

| | | | |
|---|---|---|---|
| 6,467,907 B1 * | 10/2002 | Fujieda et al. | 351/212 |
| 6,494,577 B2 * | 12/2002 | Iwanaga | 351/208 |
| 6,505,936 B1 * | 1/2003 | Holladay et al. | 351/212 |
| 6,575,572 B2 * | 6/2003 | Lai et al. | 351/211 |
| 6,655,805 B2 * | 12/2003 | Fujieda | 351/212 |
| 6,808,265 B2 * | 10/2004 | Cox | 351/219 |
| RE38,839 E * | 10/2005 | Magnante | 351/212 |
| 2002/0049431 A1* | 4/2002 | Smith et al. | 606/5 |

FOREIGN PATENT DOCUMENTS

| | | | |
|---|---|---|---|
| EP | 836830 A1 | 4/1998 | |
| EP | 0 947 158 A1 | 10/1999 | |
| EP | 947158 * | 10/1999 | 351/212 |
| EP | 947158 A1 | 10/1999 | |
| EP | 1 034 756 A2 | 9/2000 | |
| EP | 1034756 A2 | 9/2000 | |
| WO | WO-01/21061 A1 | 3/2001 | |
| WO | WO 01/21061 A1 | 3/2001 | |

* cited by examiner

KERATECTOMY DATA DETERMINING DEVICE AND KERATECTOMY DATA DETERMINING PROGRAM

TECHNICAL FIELD

The present invention relates to a corneal-ablation-data determining apparatus and a corneal-ablation-data determining program for use in keratorefractive surgery for ablating a corneal surface of a patient's eye (an eye to be operated on) to correct a refractive error.

BACKGROUND ART

There is known keratorefractive surgery for ablating a corneal surface with a laser beam in an ultraviolet wavelength range and changing its shape to correct a refractive error of a patient's eye. In a case where even aberration of the eye is to be corrected by the surgery, mainly two methods are used for calculation of a corneal ablation amount.

The first one is a method of obtaining the corneal ablation amount based on measurement data on wavefront aberration in a wide area of the patient's eye. In this method, the corneal ablation amount may be obtained using Expression 1 being an approximate expression which is conventionally known as a processing technique for an optical component.

[Expression 1]
$$P \approx \frac{\delta W}{n-1}$$

In Expression 1, $\delta W$ is wavefront aberration, n is a refractive index of an optical component to be corrected, P is a correction amount for a surface.

The second one is, as described in U.S. Pat. No. 6,033,075 (Japanese Patent Application Unexamined Publication No. Hei11-342152) and U.S. Pat. No. 6,086,204, a method of obtaining the corneal ablation amount using measurement data on objective refractive power distribution or that on wavefront aberration distribution in the wide area of the patient's eye, and data on a pre-operative corneal shape.

The corneal ablation amount is obtained by these conventional calculation methods as an ablation amount where the patient's eye is emmetropia with no aberration in a measurement optical axis direction established at the time of the measurement of the objective refractive power distribution or the wavefront aberration distribution (or a non-aberration eye which has particular refractive power in the measurement optical axis direction). However, a human eye is an eccentric optical system comprised of refractive elements such as the cornea and a crystalline lens, and the corneal shape is generally asymmetrical with respect to a visual axis. Therefore, in the conventional calculation methods for the corneal ablation amount, there is a problem that the ablation amount becomes eccentric.

In addition, in the case of additional ablation performed for correcting the patient's eye after the ablation through axial-deviated irradiation of the laser beam, there is a case where a proper corneal ablation amount cannot be obtained with the conventional calculation method for the corneal ablation amount.

The present invention has been made in view of the above circumstances and has an object to overcome the above problems and to provide a corneal-ablation-data determining apparatus and a corneal-ablation-data determining program capable of controlling corneal ablation amount distribution and expanding ablation applicability.

DISCLOSURE OF THE INVENTION

To achieve the objects and in accordance with the purpose of the present invention, as embodied and broadly described herein, the present invention has the following features.

1) A corneal-ablation-data determining apparatus for use in keratorefractive surgery for ablating a corneal surface to correct a refractive error is characterized as having input means for inputting measurement data on any one of wavefront aberration distribution and refractive power distribution of a patient's eye, decentering means for decentering a reference axis being a calculation reference for a corneal ablation amount, and calculation means for obtaining the corneal ablation amount based on the measurement data and data on eccentricity of the reference axis.

2) In the corneal-ablation-data determining apparatus according to 1), the decentering means includes means for decentering the reference axis with respect to a measurement optical axis used for measurement of any one of the wavefront aberration distribution and the refractive power distribution, and means for inputting the data on the eccentricity.

3) In the corneal-ablation-data determining apparatus according to 1), the input means inputs the measurement data on the refractive power distribution, and the calculation means obtains a post-operative corneal shape based on the measurement data on the refractive power distribution using a vector expression under the Snell's law so that an optical path inside the eye becomes the same before and after the surgery.

4) In the corneal-ablation-data determining apparatus according to 1) characterized as further having means for inputting data on a pre-operative corneal shape, the calculation means obtains a post-operative corneal shape based on the data on the pre-operative corneal shape, the measurement data, and the data on the eccentricity of the reference axis.

5) In the corneal-ablation-data determining apparatus according to 1), the calculation means obtains a direction vector of incident light into a post-operative cornea when the reference axis is decentered, and obtains a condition for a post-operative corneal shape as a normal vector of the cornea based on the direction vector.

6) A corneal-ablation-data determining program for calculating a corneal ablation amount for use in keratorefractive surgery for ablating a corneal surface to correct a refractive error, the program is characterized as making a computer to function as means for inputting measurement data on any one of wavefront aberration distribution and refractive power distribution of a patient's eye, means for inputting data on eccentricity for decentering a reference axis being a calculation reference for a corneal ablation amount with respect to a measurement optical axis used for the measurement, and calculation means for obtaining the corneal ablation amount based on the measurement data and the data on the eccentricity of the reference axis.

7) In the corneal-ablation-data determining program according to 6), the calculation means obtains a direction vector of incident light into a post-operative cornea when the reference axis is decentered, and obtains a condition for a post-operative corneal shape as a normal vector of the cornea based on the direction vector.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

BEST MODE FOR CARRYING OUT THE INVENTION

Figure 1:
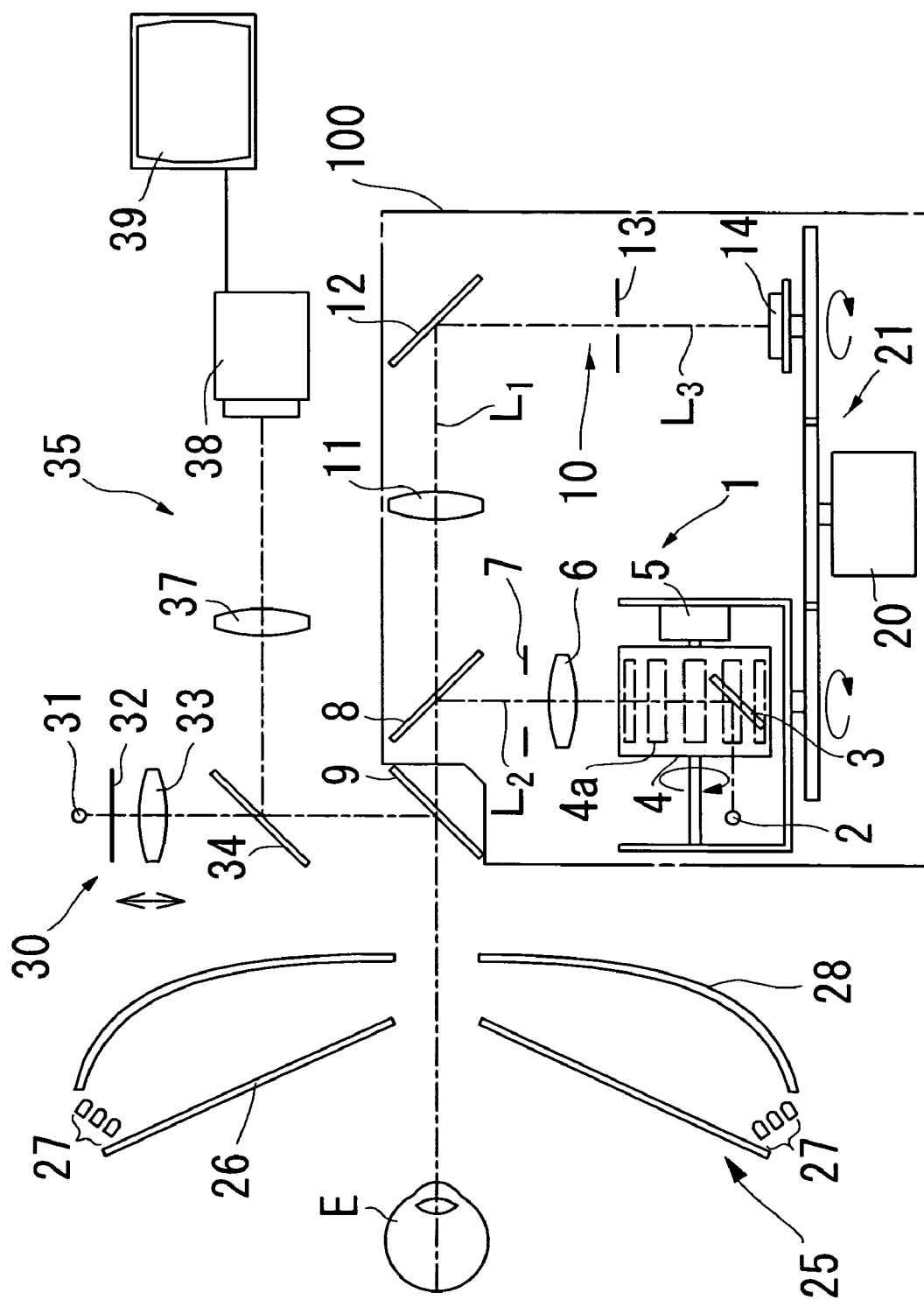
FIG. 1 is a view showing a schematic configuration of an optical system in a corneal-ablation-amount determining apparatus consistent with the present invention.

A detailed description of one preferred embodiment of the present invention will now be given referring to the accompanying drawings. FIG. 1 is a view showing a schematic configuration of an optical system in a corneal-ablation-amount determining apparatus consistent with the present invention. The optical system is roughly divided into an eye refractive power measurement optical system, a fixation target optical system and a corneal curvature measurement optical system.

(Eye Refractive Power Measurement Optical System)

Reference numeral 100 indicates the eye refractive power measurement optical system consisting of a slit light projection optical system 1 and a slit image detection optical system 10. Near infrared light emitted from a light source 2 of the projection optical system 1 is reflected by a mirror 3 to illuminate a slit opening 4a in a rotation sector 4. A motor 5 rotates the sector 4. Slit light scanned by the rotation of the sector 4 passes through a projection lens 6 and a limit diaphragm 7, and is reflected by a beam splitter 8. Then, the slit light is transmitted through a beam splitter 9 which makes an optical axis of the fixation target optical system and an observation optical system (described later) coaxial, and converges in the vicinity of a cornea Ec of a patient's eye (an eye to be examined, an eye to be operated on) E to be projected onto a fundus Ef. Besides, the light source 2 is arranged at a position conjugate with the vicinity of the cornea Ec with respect to the lens 6.

Figure 2:
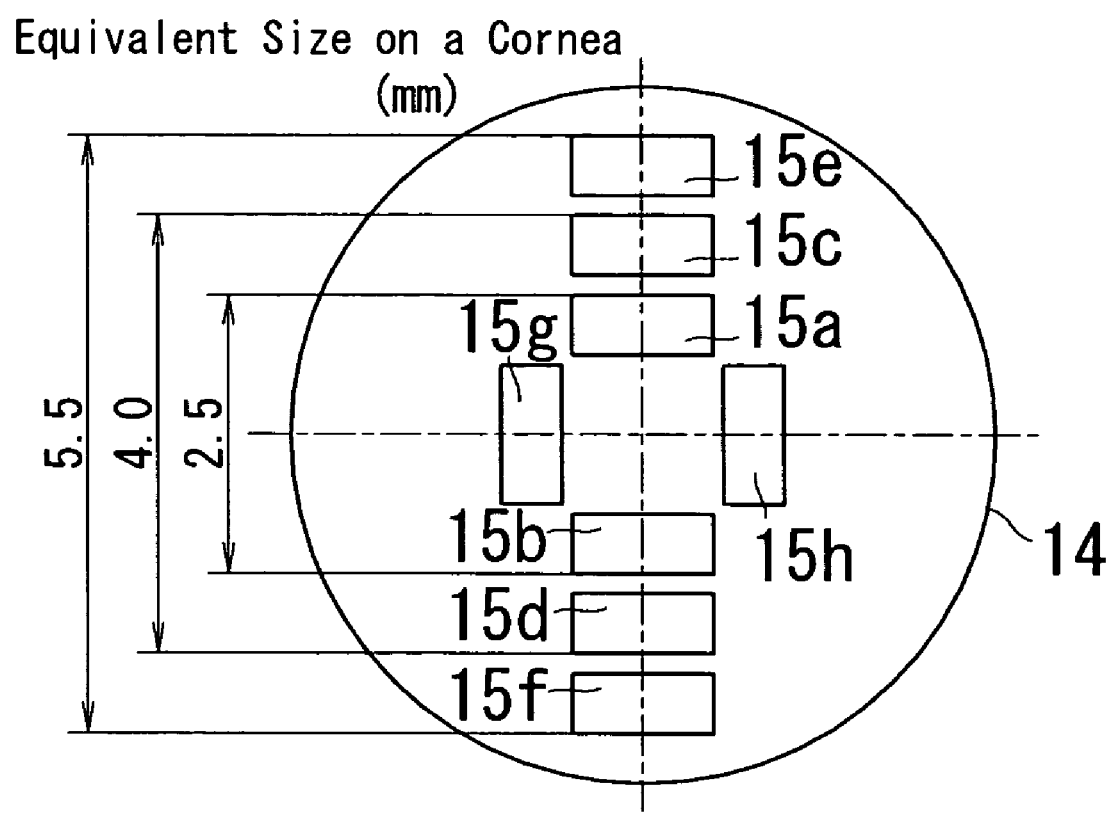
FIG. 2 is a view showing an arrangement of photodetectors in an eye refractive power measurement optical system.

The detection optical system 10 is provided with a photo-receiving lens 11 and a mirror 12 disposed on a principal optical axis L1, and a diaphragm 13 and a photo-receiving unit 14 disposed on an optical axis L3, which is formed by reflection of the mirror 12. The diaphragm 13 is arranged at a back focal point of the lens 11 via the mirror 12. (That is to say, it is arranged at a position conjugate with an emmetropic fundus.) As shown in FIG. 2, the photo-receiving unit 14 includes, on its photo-receiving surface, eight photodetectors 15a-15h arranged at positions approximately conjugate with the cornea Ec with respect to the lens 11. Among them, the photodetectors 15a-15f are positioned on a line passing through a center of the photo-receiving surface (the optical axis L3), and the photodetectors 15a and 15b, 15c and 15d, 15e and 15f, respectively, are arranged symmetrically with respect to the center of the photo-receiving surface. As for these three pairs of the photodetectors, distance in the arrangement is set so as to detect refractive power corresponding to each position in a meridian direction on the cornea Ec. (In FIG. 2, it is shown as an equivalent size on the cornea.) On the other hand, the photodetectors 15g and 15h are arranged symmetrically with respect to the optical axis L3 on a line perpendicular to the line on which the photodetectors 15a-15f are arranged.

In the measurement optical system 100 having a constitution described above, a rotation mechanism 21 consisting of a motor 20, a gear and the like rotates synchronously the light source 2 to the motor 5 in the projection optical system 1 about the optical axis L2, and the photo-receiving unit 14 about the optical axis L3. The preferred embodiment is configured so that, when the slit light is scanned on a fundus of a hyperopic eye or a myopic eye without astigmatism, the arrangement direction of the photodetectors 15a-15f is perpendicular to a longitudinal direction of the slit light (image) photo-received on the photo-receiving unit 14.

(Fixation Target Optical System)

Reference numeral 30 is the fixation target optical system, 31 is a visible light source, 32 is a fixation target, and 33 is a projection lens. The lens 33 moves in an optical axis direction to fog the eye E. A beam splitter 34 makes the optical axis of the observation optical system coaxial. The light source 31 illuminates the fixation target 32. Light from the fixation target 32 passes through the lens 33 and the beam splitter 34, and is reflected by the beam splitter 9 to head for the eye E. Thereby, the eye E may fixate the fixation target 32.

(Corneal Radius of Curvature Measurement Optical) System

The corneal radius of curvature measurement optical system consists of a target projection optical system 25 for measuring a corneal radius of curvature and a target detection optical system 35 for measuring a corneal radius of curvature. The projection optical system 25 has the following constitution. Reference numeral 26 is a conic placido plate which has an opening in a center part. Formed on the placido plate 26 is a ring-pattern, which has a number of light transmission parts and light shielding parts concentrically arranged while having the optical axis L1 as the center. Reference numeral 27 is a plurality of illumination light sources such as an LED. Illumination light emitted from the light sources 27 is reflected by a reflection plate 28 to illuminate the placido plate 26 from behind almost uniformly. The light of the ring-pattern transmitted through the transmission parts of the placido plate 26 is projected onto the cornea Ec to form a ring-pattern (placido ring) image thereon.

The detection optical system 35 is provided with the beam splitter 9, the beam splitter 34, a photographing lens 37 and a CCD camera 38. The light of the ring-pattern image formed on the cornea Ec is reflected by the beam splitters 9 and 34, and enters (is received by) an image-pickup element of the camera 38 by the lens 37. In addition, the detection optical system 35 doubles as the observation optical system, and the light of an anterior-segment image of the eye E illuminated by an anterior-segment illumination light source unillustrated enters (is received by) the image-pickup element of the camera 38. A TV monitor 39 displays the photographed anterior-segment image and the ring-pattern image.

Figure 3:
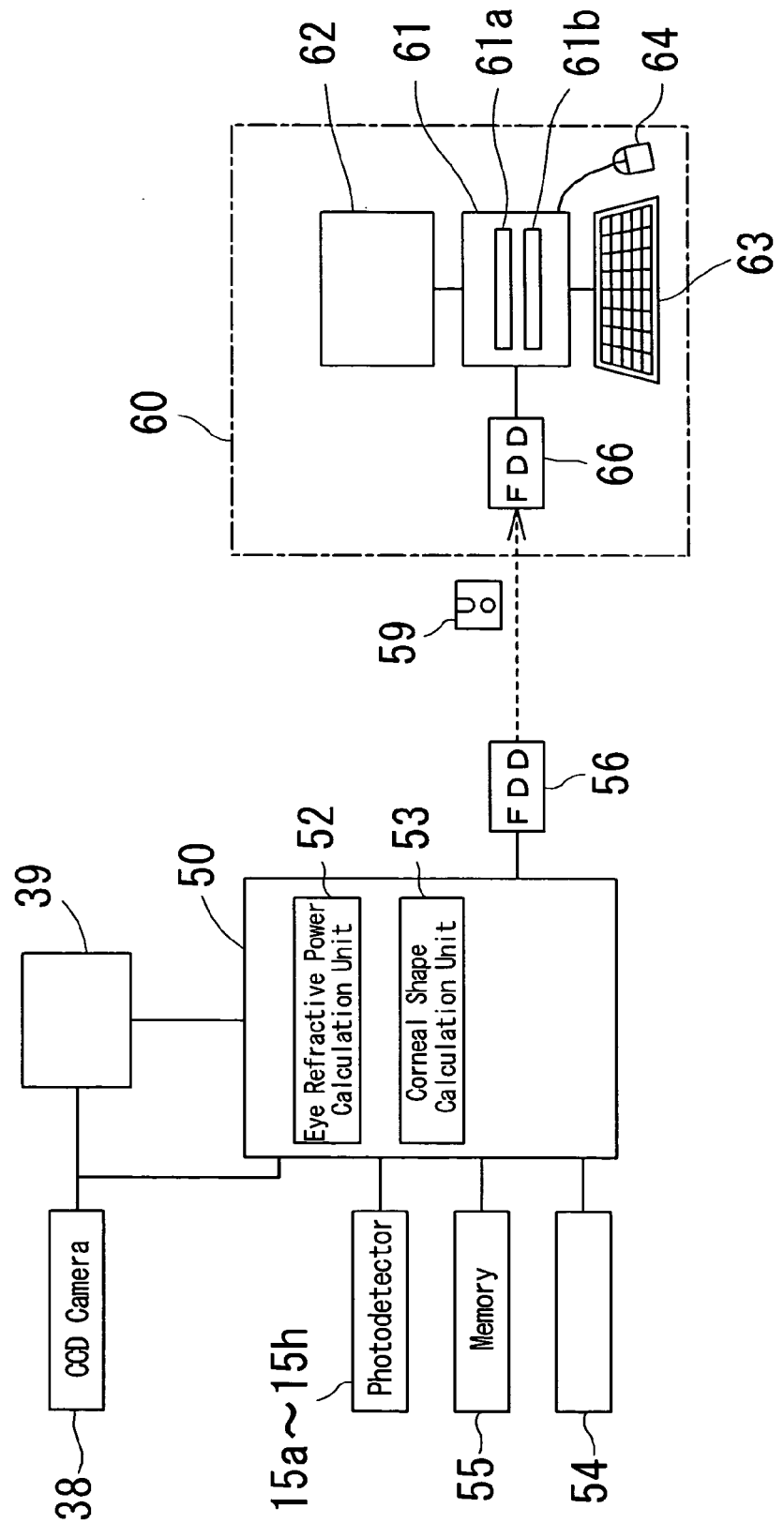
FIG. 3 is a view showing a block diagram of a control system in the corneal-ablation-amount determining apparatus.

FIG. 3 is a block diagram of a control system. A measurement system control unit 50 is connected with the photodetectors 15a-15h, the camera 38, the monitor 39, a measurement switch 54, a memory 55, an FDD (floppy disk drive) 56, and the like to control each element. The monitor 39 is formed of a touch panel, and doubles as input means. The control unit 50 is provided with a refractive power calculation unit 52 and a corneal shape calculation unit 53. Measurement data is recorded on a floppy disk 59 by the FDD 56, and inputted to a computer 60. The computer 60 is provided with a control unit 61, a color display 62, a keyboard 63, a mouse 64, an FDD 66 and the like. The control unit 61 includes a calculation unit 61a and a memory 61b which stores a control program.

Next, measurement of eye refractive power distribution and a corneal radius of curvature (a corneal shape) will be described hereinafter. A touch key on the monitor 39 is operated to place the apparatus in an eye refractive power measurement mode. An examiner performs alignment while observing the image of the anterior-segment of the eye E on the monitor 39. As for the alignment, a target for alignment unillustrated is projected onto the cornea Ec from the front of the eye E so that its corneal reflex and a reticle may have a predetermined positional relationship. In the apparatus in the preferred embodiment, the measurement optical axis (L1) is aligned with an axis connecting the corneal reflex and the fixation target. After the completion of the alignment, the measurement switch 54 is depressed and a trigger signal is generated to perform the measurement.

The eye refractive power calculation unit 52 obtains objective eye refractive power distribution based on phase difference of an output signal from each of the photodetectors in the photo-receiving unit 14. First, preliminary measurement is performed in the same manner as refractive power measurement in a conventional phase difference method, and the lens 33 is moved based on its result to fog the eye E. After that, a corneal vertex (a corneal center) in a meridian direction on which the photodetectors 15a-15f are placed is obtained based on the output signals from the photodetectors 15g and 15h which vary in accordance with movement of the slit light (image) on the photo-receiving part 14. Next, the refractive power in a corneal portion corresponding to each of the photodetectors is obtained based on the phase difference of the output signal from each of the photodetectors 15a-15f with respect to the corneal vertex (corneal center). Then, while making the projection optical system 1 and the photo-receiving unit 14 to rotate 180 degrees at a step with a predetermined angle (1 degree), the refractive power is calculated for every meridian at each step of angles to obtain the distribution of the refractive power which varies in the meridian direction. (For more details, please refer to U.S. Pat. No. 5,907,388 (Japanese Patent Application Unexamined Publication No. Hei10-108837).) Here, an eye refractive power value is obtained while taking the corneal vertex (corneal center) as reference; however, it may also be obtained while taking a spectacle-lens wearing position as the reference. Data on the objective eye refractive power obtained is stored in the memory 55.

At the time of the measurement of the corneal radius of curvature, the touch key on the monitor 39 is operated to place the apparatus in a corneal radius of curvature measurement mode. The alignment is performed in the same manner as in the eye refractive power measurement mode, and the measurement switch 54 is depressed to perform measurement. The corneal shape calculation unit 53 processes the image photographed by the camera 38 to detect an edge of the ring-pattern image. Then, each edge position with respect to the corneal vertex (corneal center) is obtained for every step of the predetermined angle (1 degree) to calculate the corneal radius of curvature. (For more details, please refer to U.S. Pat. No. 5,500,697 (Japanese Patent Application Unexamined Publication Hei7-124113) and others.) Data on the corneal radius of curvature obtained is stored in the memory 55.

When the measurement data on the objective eye refractive power and that on the corneal radius of curvature are obtained as provided above, they are inputted to the computer 60 via the floppy disk 59, and a corneal ablation amount is calculated by operating the keyboard 63, the mouse 64 and the like provided to the computer 60. Hereinafter, a calculation method of the corneal ablation amount will be described.

<Condition of Post-Operative Corneal Shape Derived from the Snell's Law>

In a case where even the aberration is corrected by the corneal ablation, it is necessary that an optical path inside the eye becomes the same before and after the ablation. Therefore, inclination of each point on a corneal surface is varied accordingly to absorb variation in an angle of incidence into the cornea. When this is expressed using Formula 1 being a vector formula under the Snell's law, Formulae 2 and 3 are obtained.

[Expression 2]  Formula 1
$$n'\vec{Q'} \times \vec{N} = n\vec{Q} \times \vec{N}$$

[Expression 3]  Formula 2
$$n_c \vec{Q}_c \times \vec{N}_{pre} = \vec{Q}_{pre} \times \vec{N}_{pre}$$

and $$n_c \vec{Q}_c \times \vec{N}_{post} = \vec{Q}_{post} \times \vec{N}_{post}$$  Formula 3

$n_c$: a refractive index of the cornea $\vec{Q}_c$: a unit direction vector of refractive light in the cornea $\vec{Q}_{pre}$: a unit direction vector of incident light into the cornea before the correction $\vec{Q}_{post}$: a unit direction vector of the incident light into the cornea after the correction $\vec{N}_{pre}$: a unit normal vector of the cornea before the correction $\vec{N}_{post}$: a unit normal vector of the cornea after the correction The vector $N_{pre}$ may be known by the corneal shape measurement. In addition, the vector $Q_{pre}$ may be obtained as a unit normal vector of wavefront aberration into which the measurement result of the above-mentioned refractive power distribution is once converted. In general, a beam emitted from a central fovea going out of the eye does not necessarily cross the measurement optical axis, because a meridian direction component is obtained in the measurement of the refractive power distribution. In order to calculate the post-operative corneal shape to obtain the vector $Q_{post}$ which is designated by using the vector $N_{pre}$ and the vector $Q_{pre}$, the following process is to be taken.

First, a vector $n_c Q_c$ is obtained using Formula 4 which is equivalent to Formula 1.

[Expression 4]  Formula 4

$$\vec{n'Q'} = n\vec{Q} + \left\{ \pm \sqrt{n'^2 - n^2 + n^2 (\vec{Q} \cdot \vec{N})^2} - \vec{Q} \cdot \vec{N} \right\} \vec{N} \begin{cases} + \cdots \vec{Q} \cdot \vec{N} \geq 0 \\ - \cdots \vec{Q} \cdot \vec{N} < 0 \end{cases}$$

In the case of Formula 2, Formula 5 is given.

[Expression 5]  Formula 5

$$n_c \vec{Q}_c = \vec{Q}_{pre} + \left\{ \pm \sqrt{n_c^2 - 1 + (\vec{Q}_{pre} \cdot \vec{N}_{pre})^2} - \vec{Q}_{pre} \cdot \vec{N}_{pre} \right\} \vec{N}_{pre} \begin{cases} + \cdots \vec{Q}_{pre} \cdot \vec{N}_{pre} \geq 0 \\ - \cdots \vec{Q}_{pre} \cdot \vec{N}_{pre} < 0 \end{cases}$$

Thereby, the vector $nQ_c$ is determined.

Next, the vector $N_{post}$ is obtained by Formula 3. Since the vector $nQ_c$ is already known and the vector $Q_{post}$ is a value to be designated, Formula 3 may be solved for the unknown vector $N_{post}$. Formula 3 is transformed to Formula 6.

[Expression 6]  Formula 6

$$(n_c \vec{Q}_c - \vec{Q}_{post}) \times \vec{N}_{post} = 0$$

As a vector product of two vectors (vectors that are not zero) is zero, they are parallel to each other. Also, the vector $N_{post}$ is a unit vector. Therefore, the vector $N_{post}$ may be expressed as Formula 7.

[Expression 7]  Formula 7

$$\vec{N}_{post} = \frac{n_c \vec{Q}_c - \vec{Q}_{post}}{|n_c \vec{Q}_c - \vec{Q}_{post}|}$$

If this is performed for each point using Formulae 5 and 7, the condition of the post-operative corneal shape may be obtained as the normal vector at each point.

Incidentally, in the present embodiment, the post-operative corneal shape is calculated so as to correct the aberration of the eye based on the measurement result of the refractive power distribution. Since the method for formulating the calculation condition for the post-operative corneal shape using the vector formula under the Snell's law as above does not perform paraxial calculation, more precise post-operative corneal shape may be obtained.

<Method for Obtaining a Unit Direction Vector of the Incident Light Into the Post-Operative Cornea ($Q_{post}$) When Eccentricity is Applied to the Post-Operative Reference Axis>

In order to use the method for obtaining the vector $N_{post}$ as above, the vector $Q_{post}$ is expressed as an expression. The measurement optical axis of the eye refractive power measurement (and the corneal shape measurement) is set as reference coordinates, and post-operative reference axis is assumed to be applied with eccentricity in shift and tilt from the reference coordinates.

Figure 4:
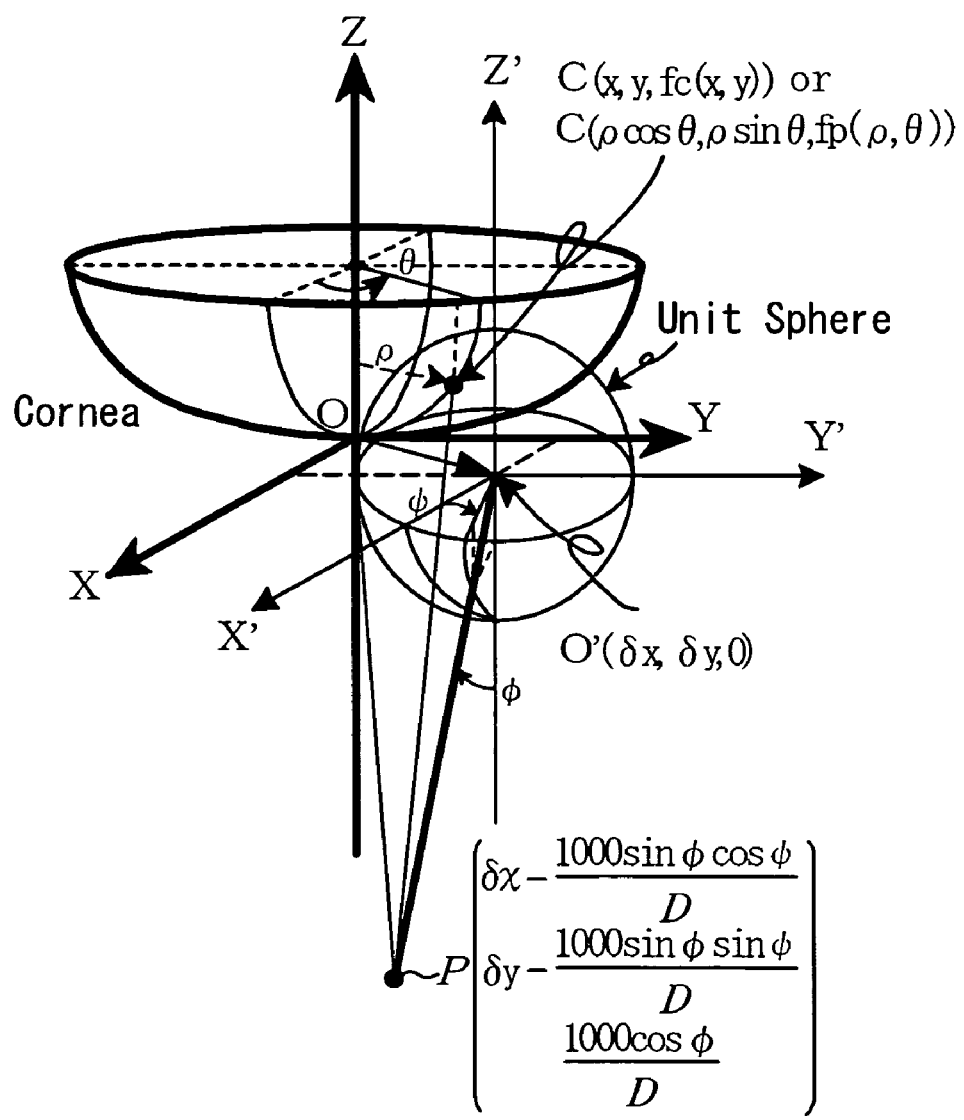
FIG. 4 is a view illustrating configuration of a coordinate system when a post-operative reference axis is decentered.

FIG. 4 is a view illustrating configuration of a coordinate system when the post-operative reference axis is decentered. In FIG. 4, an axis OZ is the measurement optical axis, and an axis PO' is the post-operative reference axis. As for the eccentricity of the post-operative reference axis PO', the shift is designated by $\delta x$ and $\delta y$, and the tilt is designated by $\phi$ and $\varphi$. In addition, assuming that the post-operative refractive power (Refractive Error) is targeted to become D[diopter] (a spherical value), Formula 8 is presented.

[Expression 8]  Formula 8

$$\vec{O'P} = -\frac{1000}{D} \begin{pmatrix} \sin\phi\cos\varphi \\ \sin\phi\sin\varphi \\ -\cos\phi \end{pmatrix}$$

Here, if the vectors $Q_{pre}$ and $Q_{post}$ for a point C on the cornea is considered, the vector $Q_{post}$ being a unit direction vector parallel to a line PC is firstly expressed as Formula 9.

[Expression 9]  Formula 9

$$\vec{Q}_{post} = \frac{\vec{PC}}{|\vec{PC}|}$$

$$= \frac{\begin{pmatrix} x - \delta x + (1000\sin\phi\cos\varphi)/D \\ y - \delta y + (1000\sin\phi\sin\varphi)/D \\ f_c(x, y) - (1000\cos\phi)/D \end{pmatrix}}{\sqrt{\begin{aligned} &\{x - \delta x + (1000\sin\phi\cos\varphi)/D\}^2 + \\ &\{y - \delta y + (1000\sin\phi\sin\varphi)/D\}^2 + \\ &\{f_c(x, y) - (1000\cos\phi)/D\}^2 \end{aligned}}}$$

$$= \frac{|D|}{D} \cdot \frac{\begin{pmatrix} \frac{(x-\delta x)D}{1000} + \sin\phi\cos\varphi \\ \frac{(y-\delta y)D}{1000} + \sin\phi\sin\varphi \\ \frac{f_c(x,y)D}{1000} - \cos\phi \end{pmatrix}}{\sqrt{\begin{aligned} &\left\{\frac{(x-\delta x)D}{1000} + \sin\phi\cos\varphi\right\}^2 + \\ &\left\{\frac{(y-\delta y)D}{1000} + \sin\phi\sin\varphi\right\}^2 + \\ &\left\{\frac{f_c(x,y)D}{1000} - \cos\phi\right\}^2 \end{aligned}}}$$

<Method for Obtaining the Post-Operative Corneal Shape>

Next, a method will be described which is for obtaining the post-operative corneal shape based on the normal vector of the post-operative cornea obtained by applying Formulae 5 and 7 to all data points.

First, the normal vector N when the corneal shape is given in an x-y coordinates form (see FIG. 4) is formulated. In this case, a position vector r at each position is expressed as Formula 10.

[Expression 10]

$$\vec{r} = x\vec{i} + y\vec{j} + f_c(x,y)\vec{k}$$  Formula 10

By partially differentiating the above formula with respect to x and y, respectively, Formula 11 is given.

[Expression 11]  Formula 11

$$\frac{\partial \vec{r}}{\partial x} = \vec{i} + \frac{\partial f_c(x,y)}{\partial x}\vec{k}, \quad \frac{\partial \vec{r}}{\partial y} = \vec{j} + \frac{\partial f_c(x,y)}{\partial y}\vec{k}$$

Accordingly, using Formula 12, the normal vector N is obtained by Formula 13.

[Expression 12]   Formula 12

$$\frac{\partial \vec{r}}{\partial x} \times \frac{\partial \vec{r}}{\partial y} = \begin{vmatrix} \vec{i} & \vec{j} & \vec{k} \\ 1 & 0 & \frac{\partial f_c(x,y)}{\partial x} \\ 0 & 1 & \frac{\partial f_c(x,y)}{\partial y} \end{vmatrix}$$

$$= -\frac{\partial f_c(x,y)}{\partial x}\vec{i} - \frac{\partial f_c(x,y)}{\partial y}\vec{j} + \vec{k}$$

[Expression 13]   Formula 13

$$\vec{N} = \frac{\partial \vec{r}}{\partial x} \times \frac{\partial \vec{r}}{\partial y} \Big/ \left| \frac{\partial \vec{r}}{\partial x} \times \frac{\partial \vec{r}}{\partial y} \right|$$

$$= \frac{1}{\sqrt{\left(\frac{\partial f_c(x,y)}{\partial x}\right)^2 + \left(\frac{\partial f_c(x,y)}{\partial y}\right)^2 + 1}} \begin{pmatrix} -\frac{\partial f_c(x,y)}{\partial x} \\ -\frac{\partial f_c(x,y)}{\partial y} \\ 1 \end{pmatrix}$$

When the corneal shape is given as a polar coordinate system ($\rho \cos\theta, \rho \sin\theta, f_p(\rho, \theta)$)(see FIG. 4), then Formula 14 is presented.

[Expression 14]

$$\vec{r} = \rho\cos\theta\,\vec{i} + \rho\sin\theta\,\vec{j} + f_p(\rho,\theta)\,\vec{k}$$   Formula 14

$\vec{r}$ : a position vector
$\vec{i}$ a unit vector in the x direction
$\vec{j}$ a unit vector in the y direction
$\vec{k}$ a unit vector in the z direction Accordingly, Formula 15 is obtained.

[Expression 15]   Formula 15

$$\frac{\partial \vec{r}}{\partial \rho} = \cos\theta\,\vec{i} + \sin\theta\,\vec{j} + \frac{\partial f_p(\rho,\theta)}{\partial \rho}\vec{k},$$

$$\frac{\partial \vec{r}}{\partial \theta} = -\rho\sin\theta\,\vec{i} + \rho\cos\theta\,\vec{j} + \frac{\partial f_p(\rho,\theta)}{\partial \theta}\vec{k}$$

From Formula 15, Formula 16 is given.

[Expression 16]   Formula 16

$$\frac{\partial \vec{r}}{\partial \rho} \times \frac{\partial \vec{r}}{\partial \theta} = \begin{vmatrix} \vec{i} & \vec{j} & \vec{k} \\ \cos\theta & \sin\theta & \frac{\partial f_p(\rho,\theta)}{\partial \rho} \\ -\rho\sin\theta & \rho\cos\theta & \frac{\partial f_p(\rho,\theta)}{\partial \theta} \end{vmatrix} =$$

$$\left(\frac{\partial f_p(\rho,\theta)}{\partial \theta}\sin\theta - \rho\frac{\partial f_p(\rho,\theta)}{\partial \rho}\cos\theta\right)\vec{i} -$$

$$\left(\frac{\partial f_p(\rho,\theta)}{\partial \theta}\cos\theta + \rho\frac{\partial f_p(\rho,\theta)}{\partial \rho}\sin\theta\right)\vec{j} + \rho\vec{k}$$

Therefore, the normal vector N is expressed as Formula 17.

[Expression 17]   Formula 17

$$\vec{N} = \frac{\partial \vec{r}}{\partial \rho} \times \frac{\partial \vec{r}}{\partial \theta} \Big/ \left|\frac{\partial \vec{r}}{\partial \rho} \times \frac{\partial \vec{r}}{\partial \theta}\right| = \cdots = \frac{1}{\sqrt{\left(\rho\frac{\partial f_p(\rho,\theta)}{\partial \rho}\right)^2 + \left(\frac{\partial f_p(\rho,\theta)}{\partial \theta}\right)^2 + \rho^2}} \begin{pmatrix} \frac{\partial f_p(\rho,\theta)}{\partial \theta}\sin\theta - \rho\frac{\partial f_p(\rho,\theta)}{\partial \rho}\cos\theta \\ -\frac{\partial f_p(\rho,\theta)}{\partial \theta}\cos\theta - \rho\frac{\partial f_p(\rho,\theta)}{\partial \rho}\sin\theta \\ \rho \end{pmatrix}$$

Besides, even if the data on the corneal shape obtained through the corneal shape measurement is in the polar coordinate system form, Formula 17 cannot be directly used. As a corneal height $f_p(\rho, \theta)$ is necessary to be partially differentiated with respect to $\theta$ in order to use Formula 17, a radius direction position $\rho$ shall be constant data. This is because, since $\rho$ is a detection edge position for the ring pattern image, it generally varies according to angles. Therefore, in order to obtain the normal vector $N_{pre}$ of the pre-operative corneal shape, Formula 17 is used after the pre-operative corneal shape is converted to the polar coordinate system data form in which $\rho$ does not depend on the angles by means of interpolation. Otherwise, Formula 13 is used after the pre-operative corneal shape is converted to the x-y rectangular coordinates system form.

Next, a method for calculating the shape based on the normal vector of the post-operative cornea obtained according to Formulae 5 and 7 will be described hereinafter. Assume that the normal vector N is obtained as the following components.

[Expression 18]   Formula 18

$$\vec{N} \equiv \begin{pmatrix} N_x \\ N_y \\ N_z \end{pmatrix}$$

Then, Formulae 19 and 20 hold for Formulae 17 and 18.

[Expression 19]   Formula 19

$$N_x \sin\theta - N_y \cos\theta =$$

$$\frac{\partial f_p(\rho,\theta)}{\partial \theta} \Big/ \sqrt{\left(\rho \frac{\partial f_p(\rho,\theta)}{\partial \rho}\right)^2 + \left(\frac{\partial f_p(\rho,\theta)}{\partial \theta}\right)^2 + \rho^2} =$$

$$\frac{N_z}{\rho} \frac{\partial f_p(\rho,\theta)}{\partial \theta}$$

[Expression 20]   Formula 20

$$-N_x \cos\theta - N_y \sin\theta =$$

$$\rho \frac{\partial f_p(\rho,\theta)}{\partial \rho} \Big/ \sqrt{\left(\rho \frac{\partial f_p(\rho,\theta)}{\partial \rho}\right)^2 + \left(\frac{\partial f_p(\rho,\theta)}{\partial \theta}\right)^2 + \rho^2} =$$

$$N_z \frac{\partial f_p(\rho,\theta)}{\partial \rho}$$

Therefore, by arranging Formulae 19 and 20, formulae 21 and 22 may be obtained.

[Expression 21]   Formula 21

$$\therefore \frac{1}{\rho} \frac{\partial f_p(\rho,\theta)}{\partial \theta} = \frac{N_x \sin\theta - N_y \cos\theta}{N_z}$$

[Expression 22]   Formula 22

$$\therefore \frac{\partial f_p(\rho,\theta)}{\partial \rho} = \frac{-N_x \cos\theta - N_y \sin\theta}{N_z}$$

Formula 22 is used for calculating the post-operative corneal shape. When the following recurrence formula in the meridian direction:

[Expression 23]   Formula 23

$$f_{p,i}(\rho,\theta) = \left(\frac{\partial f_p(\rho,\theta)}{\partial \rho}\right)_i \Delta\rho + f_{p,i-1}(\rho,\theta), \; f_{p,0}(\rho,\theta) = 0$$

is substituted by Formula 22 and calculated in order, the shape in the meridian direction may be obtained. Therein, $\Delta\rho$ is an interval of data in a radius direction perpendicular to the measurement optical axis of the measurement optical system shown in FIG. 1. Further, fp, o($\rho$, $\theta$)=0 is set so that the height on the measurement optical axis becomes 0. If the above calculation is performed for every meridian, the whole corneal shape may be constituted.

When the post-operative corneal shape is obtained as above, the ablation amount for each point may be calculated in a range on which an optical zone is set by comparing the post-operative corneal shape to the data on the corneal shape obtained from the corneal shape measurement.

Figure 5:
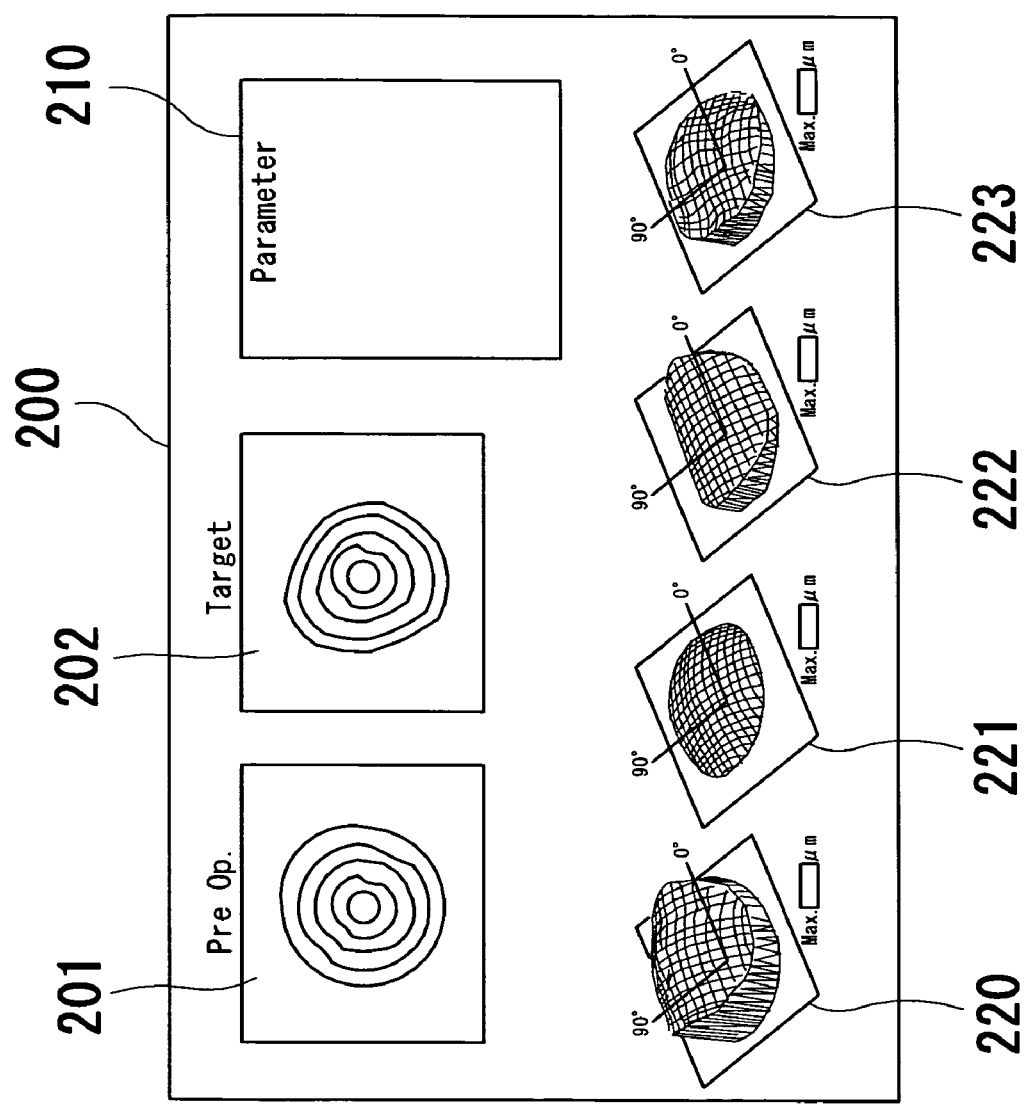
FIG. 5 is a view illustrating an example of a display of a simulation map at the time of calculation of a corneal ablation amount.

Next, ablation amount calculation operation by the computer 60 will be described. When the measurement data on the objective eye refractive power and that on the corneal shape are inputted to the control unit 61, and a control program for the ablation amount calculation by the control unit 61 is executed, a simulation map display 200 as shown in FIG. 5 is displayed on the display 62. The keyboard 63 or the mouse 64 is operated to input desired refractive power, a size of a range for correction (sizes of the optical zone and a transition zone), data on the shift and tilt of an eccentric parameter to an input parameter unit 210. The calculation unit 61a calculates the ablation amount under a condition based on the inputted data.

Displayed on the upper-left of the display 200 are a color map 201 of the pre-operative corneal shape and a color map 202 of the post-operative corneal shape. On the lower portion of the display 200, the simulated ablation amount distributions are displayed three-dimensionally. A display map 220 shows a shape map of a whole ablation amount, and displayed as height difference between the pre-operative corneal shape and the post-operative corneal shape. A display map 221 shows a shape map for which only a spherical component (axisymmetric component) is extracted. A display map 222 shows a shape map for which only a cylindrical component (symmetric component with respect to a plane) is extracted. A display map 223 shows a shape map for which only an irregular astigmatic component (irregular component) being an asymmetric component is extracted. The calculation unit 61a obtains the irregular astigmatic component as a remaining component after the spherical and cylindrical components are subtracted from the distribution data on the whole ablation amount. When one of the display maps 220-223 is designated with the mouse, it becomes observable as a sectional shape in an arbitrary meridian direction. Further, a maximum ablation amount value is displayed under each of the display maps 220-223 as a numerical value.

Besides, assume that the shape map initially calculated and displayed is simulated without inputting the eccentric parameter, and the irregular astigmatic component displayed in the display map 223 mainly exists in an eccentric direction. As for setting of the eccentric parameter in such a case, for example, a value of the tilt is determined based on a position and a size of the eccentricity in the irregular astigmatic component so as to reduce the irregular astigmatic component. Also, a value of the shift is moved to a pupil center so as to be in alignment with an axis at the time of the ablation.

When the eccentric parameter is inputted, the calculation unit 61a calculates the post-operative corneal shape, and a result thereof is again displayed on the display 200 as the simulation map. An operator controls the corneal ablation amount distribution with such simulation to make judgment as to whether the eccentricity of an ablation amount calculation reference axis is appropriate or not. Incidentally, the eccentricity of the reference axis for the ablation amount calculation may be automatically determined by the calculation by the calculation unit 61a so that the asymmetric irregular astigmatic component becomes smaller than a predetermined permissible value, instead of inputting the eccentric parameter by the operator. As a result of the simulation of the ablation amount distribution, if the post-operative corneal shape is favorable, the obtained data may be recorded and stored in a floppy disk by the FDD 66 to be used by the corneal surgery apparatus.

Figure 6:
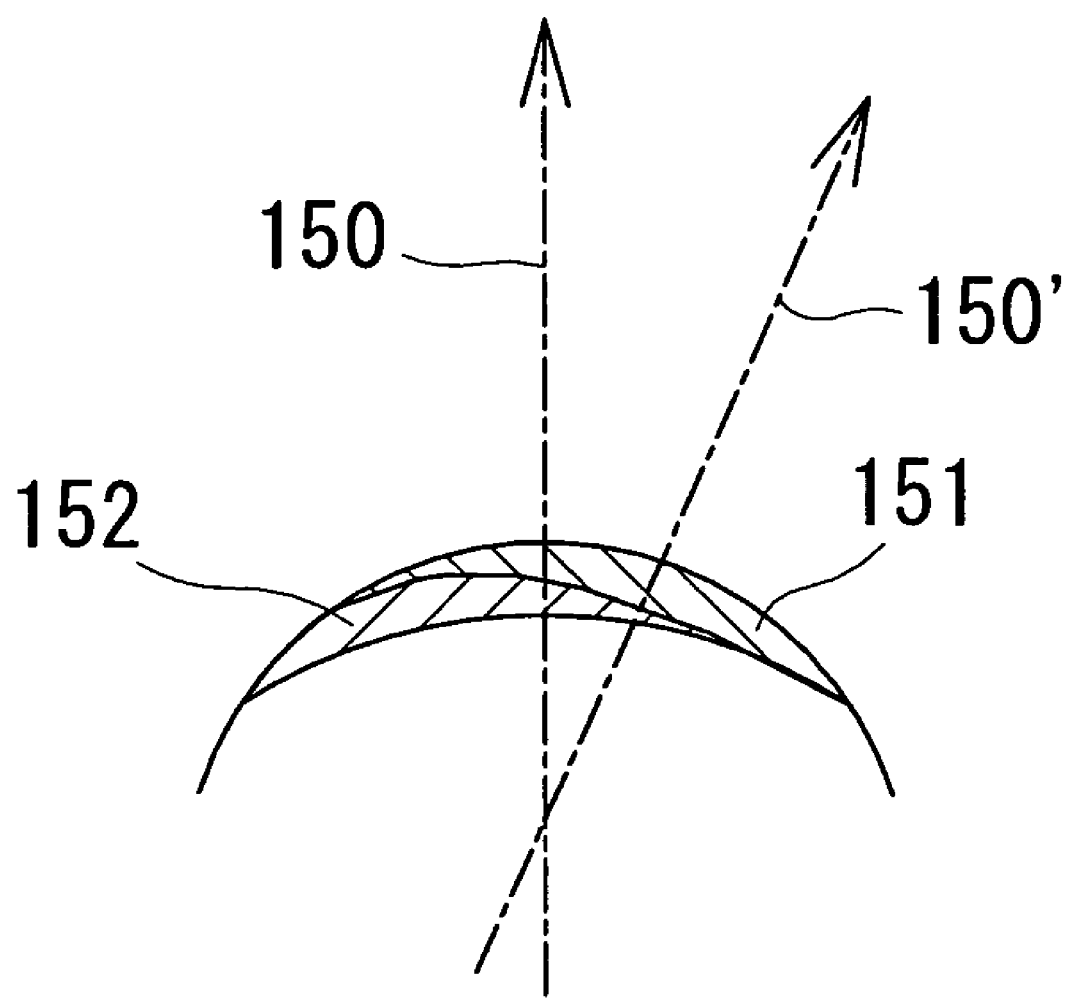
FIG. 6 is a view describing a case where additional ablation is performed on a patient's eye after ablation through axial-deviated irradiation.

Further, in a case where the additional ablation for correction is performed on the post-ablative eye onto which the laser beam has been irradiated with its axis deviated, it is particularly advantageous if the reference axis for the ablation amount calculation is decentered. For example, assume that, as shown in FIG. 6, the axial deviation occurs with respect to a measurement optical axis direction 150 (, which may be regarded as the approximate visual axis direction) at the time of the previous ablation, and an area 151 is ablated. If the measurement optical axis with respect to the eye is not varied from the pre-operative condition, the calculation is to be performed so as to ablate an area 152 at the time of the additional ablation. However, the actual result is that the area 151 which has already been ablated is mainly ablated, and the ablation is not allowed due to poor corneal thickness. Investigation on this problem revealed that the visual axis direction of the eye was decentered from a pre-operative direction 150 to a direction 150' due to the axial-deviated irradiation, and the measurement was performed under such a condition. This is appreciated from the fact that the human eye is the eccentric optical system consisting of a plurality of refractive elements. In such a case, the data for decentering the reference axis for the ablation amount calculation is inputted so as to mainly ablate the area 152. The ablation on the area 152 enables correcting the previous axial-deviated irradiation, and making the shape to be approximately in the state of initially desired one. Thus, the corneal ablation amount may be reduced, and ablation applicability may be expanded even for the eye to which the ablation has not been applicable.

In the preferred embodiment as above, the apparatus for measuring the eye refractive power distribution is utilized, and the data on the corneal ablation amount is obtained based on the measurement data. However, the present invention may naturally be applied to a case where the data on the corneal ablation amount is obtained based on the measurement data on the wavefront aberration distribution. As an example of the measurement of the wavefront aberration distribution, a method may be used where an image of a light source is projected onto a fundus of the patient's eye, and a reflection light from the fundus forms an image on an image sensor via a number of microlens arrays arranged at positions conjugate with a pupil to measure a wavefront of the light refracted in a cornea of the patient's eye based on image forming information. (See U.S. Pat. No. 6,086,204 and others.) The measurement of the refractive power distribution and that of the wavefront aberration distribution are different from each other in a form of presentation of the measurement results; however, those are the same in that the optical aberration of the eye is measured. As the vector $Q_{pre}$ (the unit direction vector of the incident light into the pre-operative cornea) expressed in Formulae 2 and 5 may be obtained via the wavefront aberration of the eye, the present invention may be applied for calculating the corneal ablation amount also in the case of the measurement of the wavefront aberration distribution.

In addition, in a method where the corneal ablation amount is calculated using an approximate expression which is known as a processing technique for an optical component, based on the measurement of the wavefront aberration of the whole eye without using the data on the corneal shape (although deviation at a peripheral part becomes greater since the approximate expression is used), the ablation amount distribution may be controlled by applying the method of decentering the reference axis for the ablation amount calculation.

INDUSTRIAL APPLICABILITY

As described above, according to the present invention, the corneal ablation amount distribution may be controlled. Therefore, unnecessary corneal ablation amount is reduced, and the ablation applicability may be expanded.

The invention claimed is:

1. A corneal-ablation-data determining apparatus for use in keratorefractive surgery for ablating a cornea of an eye to correct a refractive error of the eye, the apparatus comprising:

measurement data input means for inputting first measurement data on any one of wavefront aberration distribution of a pre-operative eye and eye refractive power distribution of a the pre-operative eye and second measurement data on a corneal surface shape of the pre-operative eye;

corneal-ablation amount calculation means for calculating a corneal ablation amount based on the input first and second measurement data; and parameter input means for inputting a parameter for tilting a direction of a visual axis of a post-operative eye with respect to a direction of a visual axis of the pre-operative eye, wherein the corneal-ablation-amount calculation means calculates a corneal ablation amount by tilting the visual axis direction of the post-operative eye based on the input parameter so that a correction power which is caused by the corneal ablation amount calculated by tilting the visual axis direction of the post-operative eye corresponds to a correction power which is caused by a corneal ablation amount calculated without tilting the visual axis direction of the post-operative eye.

2. The corneal-ablation-data determining apparatus according to claim 1, wherein the corneal-ablation-amount calculation means calculates a direction vector of incident light into each position on the cornea of the post-operative eye based on the input first and second measurement data, calculates a normal vector of each position on the cornea of the post-operative eye based on the direction vector, calculates a corneal surface shape of the post-operative eye based on the normal vector, and calculates the corneal ablation amount based on the second measurement data and the corneal surface shape data of the post-operative eye so that an optical path of the incident light inside the post-operative eye becomes the same as an optical path of the incident light inside the pre-operative eye; and the parameter input means inputs the parameter for tilting the direction of the visual axis of the post-operative eye with respect to the direction of the visual axis of the pre-operative eye to determine the direction vector.

3. The corneal-ablation-data determining apparatus according to claim 1, further comprising display means for displaying a simulation screen of the corneal ablation amount calculated based on the input parameter.

\* \* \* \* \*

UNITED STATES PATENT AND TRADEMARK OFFICE
CERTIFICATE OF CORRECTION

PATENT NO. : 7,255,440 B2  
APPLICATION NO. : 10/476246  
DATED : August 14, 2007  
INVENTOR(S) : Masaaki Hanebuchi Page 1 of 1

It is certified that error appears in the above-identified patent and that said Letters Patent is hereby corrected as shown below:

Title Page:
Item (54) and col. 1, lines 1-3, should be read as follows:
-- CORNEAL-ABLATION-DATA DETERMINING APPARATUS AND A CORNEAL-ABLATION-DATA DETERMINING SYSTEM --.

Signed and Sealed this

Thirteenth Day of May, 2008

JON W. DUDAS
*Director of the United States Patent and Trademark Office*